United States Patent
Itzel et al.

(10) Patent No.: US 8,951,212 B2
(45) Date of Patent: Feb. 10, 2015

(54) METHOD FOR MONITORING A CHILDBIRTH PROCESS

(75) Inventors: Johan Itzel, Danderyd (SE); Eva Itzel, Danderyd (SE)

(73) Assignee: Obstecare AB, Kista (SE)

(*) Notice: Subject to any disclaimer, the term of this patent is extended or adjusted under 35 U.S.C. 154(b) by 215 days.

(21) Appl. No.: 13/442,144

(22) Filed: Apr. 9, 2012

(65) Prior Publication Data
US 2012/0232428 A1 Sep. 13, 2012

Related U.S. Application Data

(63) Continuation of application No. 11/569,510, filed as application No. PCT/US2005/022670 on Jun. 28, 2005, now Pat. No. 8,172,767.

(60) Provisional application No. 60/521,814, filed on Jul. 7, 2004.

(51) Int. Cl.
| | | |
|---|---|---|
| *A61B 5/103* | (2006.01) | |
| *G06F 19/00* | (2011.01) | |
| *A61B 5/00* | (2006.01) | |
| *A61B 5/107* | (2006.01) | |
| *A61B 10/00* | (2006.01) | |

(52) U.S. Cl.
CPC .......... *G06F 19/3481* (2013.01); *A61B 5/1076* (2013.01); *A61B 10/0048* (2013.01); *A61B 5/00* (2013.01); *A61B 10/0045* (2013.01)
USPC ........................................................ 600/588

(58) Field of Classification Search
USPC ................. 600/588; 482/5; 514/557, 558
See application file for complete search history.

(56) References Cited

U.S. PATENT DOCUMENTS

| | | |
|---|---|---|
| 4,951,680 A | 8/1990 | Kirk et al. |
| 5,377,673 A | 1/1995 | Van Dell et al. |

(Continued)

FOREIGN PATENT DOCUMENTS

| | | |
|---|---|---|
| WO | 9212426 A1 | 7/1992 |
| WO | 02058537 A2 | 8/2002 |
| WO | 0534762 A1 | 4/2005 |

OTHER PUBLICATIONS

Garry, David et al. "A comparison of rapid amniotic fluid markers in the prediction of microbial invasion of the uterine cavity and preterm delivery" American Journal of Obstetrics and Gynecology. Nov. 1996; pp. 1336-1341.*

(Continued)

*Primary Examiner* — Max Hindenburg
*Assistant Examiner* — Renee Danega
(74) *Attorney, Agent, or Firm* — Pierce Atwood LLP; Kevin M. Farrell

(57) ABSTRACT

The method is for monitoring a childbirth process of a pregnant woman. A plurality of cervix dilatation data and fetal positioning data are obtained and fed to a device. A plurality of lactate concentrations is measured at time intervals. The measured lactate concentrations are shown on a display of the device at the time intervals to show a trend of the lactate concentrations. The cervix dilation data and the fetal positioning data are also shown on the display. The lactate concentrations are evaluated to determine whether the lactate concentrations are rising to indicate that an individual lactate threshold value of the pregnant woman has been exceeded. The medical practitioner may also evaluate the cervix dilation data and the fetal positioning data.

16 Claims, 2 Drawing Sheets

(56) References Cited

U.S. PATENT DOCUMENTS

2004/0078219 A1 4/2004 Kaylor et al.
2004/0100376 A1 5/2004 Lye et al.
2006/0180161 A1 8/2006 Itzel

OTHER PUBLICATIONS

Esim, Esra et al. "Diagnosis of premature rupture of membranes by identification of B-HCG in vaginal washing fluid" European Journal of Obstetrics and Gynecology and Reproductive Biology. Mar. 26, 2003; pp. 37-40.*

Yoshioka et al.; The Changes of Glucose and Organic Acids in the Amniotic Fluid During Labor; Journal of Japan Society of Neonatal Medicine; vol. 19; No. 1; pp. 88-94; Mar. 30, 1983.

Nordström et al.; Fetal and Maternal Lactate Increase During Active Second Stage of Labour; British Journal of Obstetrics and Gynaecology; vol. 108; pp. 263-268; Mar. 2001.

* cited by examiner

METHOD FOR MONITORING A CHILDBIRTH PROCESS

RELATED APPLICATIONS

This application is a continuation of U.S. patent application Ser. No. 11/569,510 filed Nov. 22, 2006, which is a U.S. National Stage application of International Application No. PCT/US2005/022670 filed Jun. 28, 2005, which claims the benefit of U.S. Provisional Patent Application No. 60/521,814 filed Jul. 7, 2004, the entire contents of which are incorporated herein.

BACKGROUND

The present invention relates to a method for monitoring a childbirth process of a pregnant woman.

One problem in today's delivery methods is that women suffer from dystocya during labor. This could result in that the delivery does not progress as desired and that the labor is drawn out without a successful natural childbirth. The pregnant woman may become frustrated and it may be necessary to use methods such as, vacuum, forceps or caesarean to deliver the baby. The dystocya of the pregnant woman may also expose the fetus to injury and fatigue.

The lactate concentration in the blood of the fetus has been measured in the past to control that the fetus does not suffer from oxygen deficiency. However, the lactate concentration in the fetus does not indicate the condition of the pregnant woman. There is a need to more effectively determine and control the condition of woman suffering from dystocya at an early stage to avoid unnecessary labor before using surgical and alternative childbirth methods.

There is also a need for an effective apparatus to be able to determine the above-outlined conditions. In addition to the above needs, the apparatus should also handle at least cervix dilatation data, fetal positioning data and fetal lactate and pH measurements. Apart from measuring, entering and displaying the information from the respective methods and sensors, the apparatus should provide a decision guiding function. The decision function should provide the tending obstetrician and midwife advice on how to act in different situations. The advice should be based on established science. The advice should include functions to prompt for needed measurements and to prompt for new measurements after a given time. It should also indicate needed actions like early instrumental delivery.

SUMMARY

The method of the present invention provides a solution to the above-outlined problems. More particularly, the method is for monitoring a childbirth process of a pregnant woman. A plurality of cervix dilatation data and fetal positioning data are obtained and fed to a measurement and/or presentation device. A plurality of lactate concentrations is measured at time intervals. The measured lactate concentrations are shown on a display of the device at the time intervals to show a trend of the lactate concentrations. The cervix dilation data and the fetal positioning data are also shown on the display. The lactate concentrations are evaluated to determine whether the lactate concentrations are rising to indicate that an individual lactate threshold value of the pregnant woman has been exceeded. The medical practitioner may also evaluate the cervix dilation data and the fetal positioning data.

DETAILED DESCRIPTION

Figure 1:
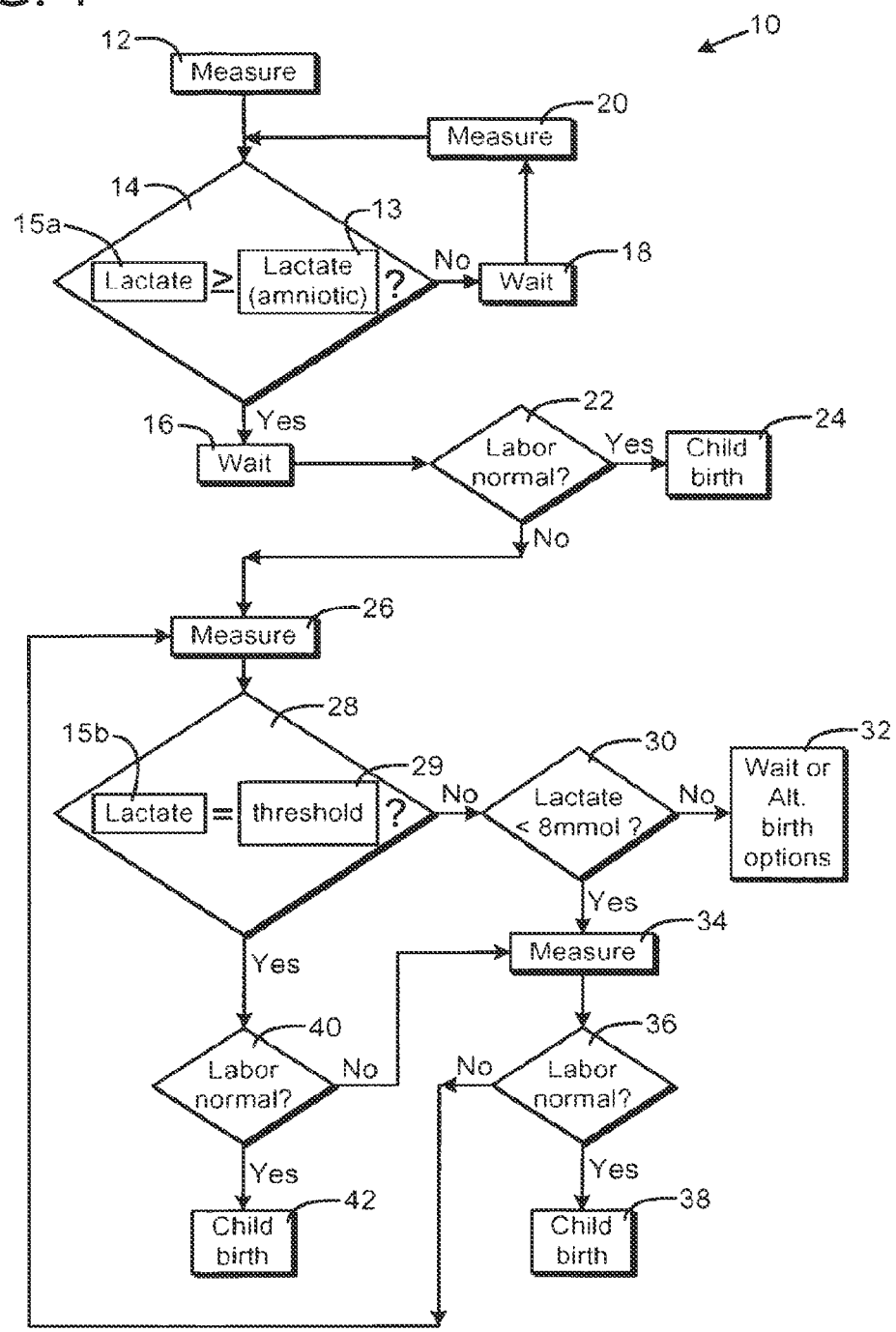
FIG. 1 is a schematic flow chart showing some of the steps of the method of the present invention.

With reference to FIG. 1, the method 10 of the present invention includes a measuring step 12 that measures a lactate concentration 15a in fluids, such as vaginal fluids, in connection with pregnancy to determine whether the amniotic fluids have passed or are in the process of being passed from the amnion. In general, the uterus muscle of pregnant women produces lactate so that the lactate concentration of the vaginal fluids may be measured to provide a measurement of the amount of lactate produced by the uterus muscle. Non-pregnant women often have no or very little lactate in the vaginal fluids.

If the lactate concentration 15a is higher than a predetermined lactate concentration 13, such as 4-5 mmol/l, more preferably higher than 4.5 mmol/l, as indicated in a comparison step 14 then it may be concluded that the membrane has ruptured and amniotic fluids likely have passed and that the childbirth labor is likely to start after a waiting period 16. It is to be understood that the 4-5 mmol/l is an illustrative example that applies to most women and that the invention is not limited to the values used in the examples.

If the lactate concentration is lower than 4.5 mmol/l then there is a high likelihood that the amniotic fluids are still contained within the amnion. The lactate concentration may again be measured in a measuring step 20 after a waiting period 18. It is again determined in the comparison step 14 whether the lactate concentration is more or less than 4.5 mmol/l. If the lactate concentration is again below 4.5 mmol/l, a second measuring may be conducted later and the measuring may be repeated at suitable time intervals until the lactate concentration exceeds 4.5 mmol/l or it is obvious that the amniotic fluids have passed.

As indicated above, if the lactate concentration measured in the measuring step 12 is above 4.5 mmol/l, the next step is to wait for about two days or so to see if the woman starts the labor by herself. In a determining step 22, it is determined whether the labor has started or not. If the labor has started and is progressing normally then the childbirth procedure 24 may proceed. If it is determined in the determining step 22 that the labor has not started or the labor is not progressing normally, a lactate concentration 15b is measured in a measuring step 26.

In a comparison step 28 it is then determined if the lactate concentration 15b as measured in the measuring step 26 is within a lactate threshold interval 29 that may be about 8-10 mmol/l. If the lactate concentration as measured in the step 26 is not within the threshold interval 29, then it is determined in a comparison step 30 whether the lactate concentration is less than the threshold interval 29 or about 8 mmol/l. If the lactate concentration as measured in step 26 is greater than the threshold interval 29 then a waiting step 32, such as a couple of hours, may start to see if the labor progress normally. If labor does not progress normally, alternative childbirth options may be considered such as caesarean, forceps or the use of suction cups that are connected to vacuum to draw out the baby. An important feature of the present invention is that the monitoring of the lactate concentration may be used to predict whether the woman is likely to give a natural birth or not without forcing the pregnant woman to go through long and agonizing efforts to give birth. It is therefore possible to use alternative childbirth options at a relatively early stage. It is to be understood that the 8-10 mmol/l is an illustrative example that applies to most women and that the invention is not limited to the values used in the examples.

If the lactate concentration, as measured in step 26, is less than the threshold interval 29, then the woman may be stimulated with drugs or other aids to give birth in a stimulation step 34. In a determining step 36, it may be determined if the labor is progressing normally. If the labor is progressing normally the woman may proceed to give birth 38. If the labor is not progressing normally, the lactate concentration may again be measured in the measuring step 26 and the process continues in the comparison step 28, as described above.

If it is determined in the comparison step 28 that the lactate concentration, as measured in step 26, is at the threshold interval 29, such as between 8-10 mmol/l, then it is determined whether the labor is progressing normally in a determining step 40. If labor is progressing normally, the woman may proceed to give birth 42. If labor is not progressing normally, the woman may be stimulated to give birth in the stimulation step 34 and the process continues to the determining step 36, as described above.

The various processing loops may continue until the woman either gives birth by herself or is subjected to alternative childbirth options. As indicated above, an important feature of the present invention is that the woman may be prevented from agonizing and long childbirth efforts before alternative childbirth options are used. Alternative childbirth options may be used at an earlier stage when the lactate concentration indicates that the uterus muscle is operating above the lactate threshold without resulting in a natural childbirth.

Another important feature of the present invention is to use a measuring and presentation device to effectively present the measured lactate values together with the time lapsed. The depicted time intervals could be both on a relative time (time from start) or absolute time (time of day) to indicate the trends of the measured lactate values. In addition, the device may also be used to measure lactate levels in the fetus such as in the scalp blood of the fetus. The device may also be used to present the how far down in the pelvis the head of the fetus has penetrated and the dilation of the cervix.

Figure 2:
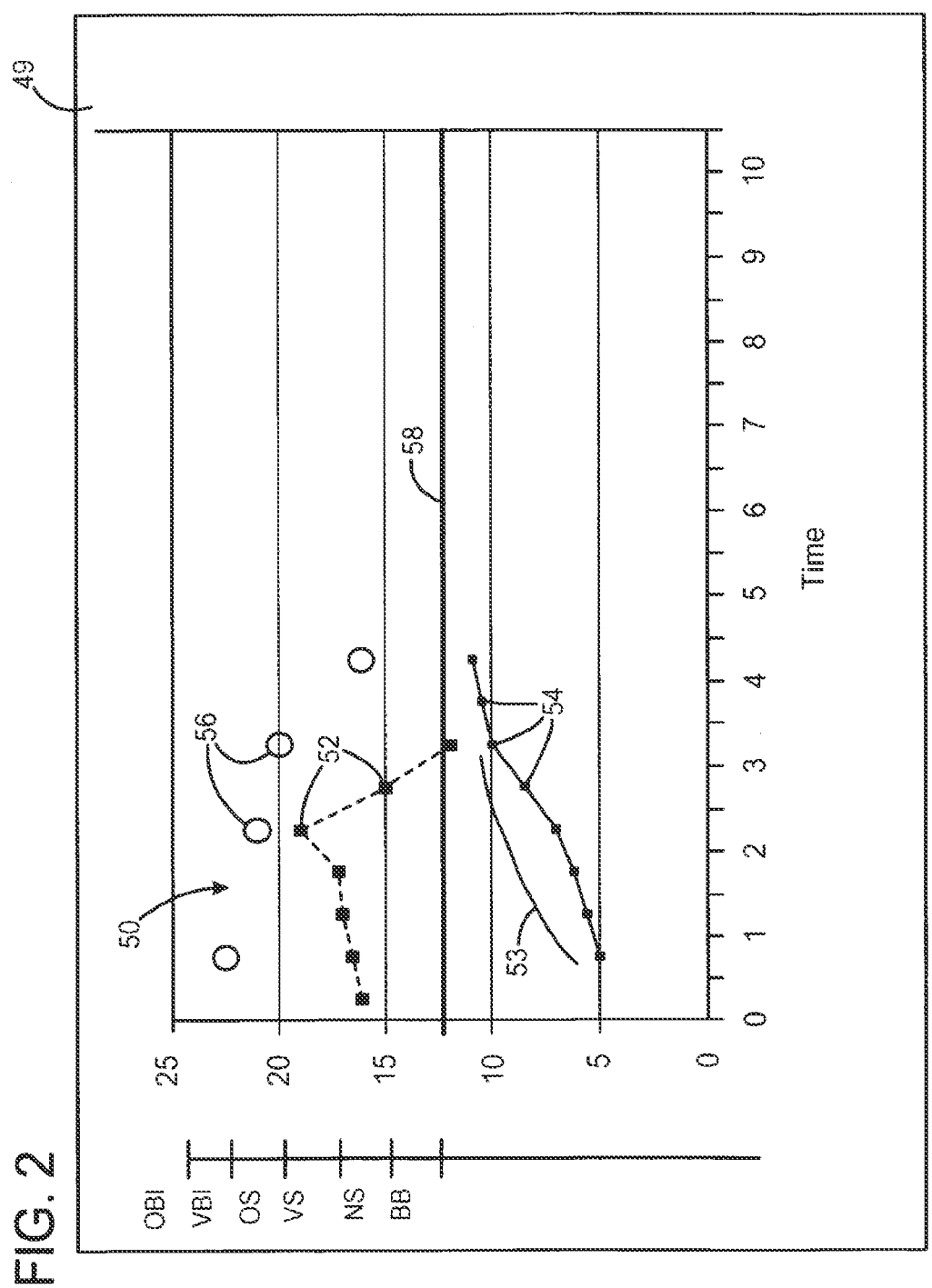
FIG. 2 is a schematic illustration of graphical representation of measured data.

FIG. 2 is a display 50 is an illustrative example that shows lactate data 52 of the pregnant woman over time, lactate data 53 of the fetus, cervix dilation data 54 and fetal head positioning data 56. For example, the lactate data 52 shows an upward trend until the addition of stimulation substances to the pregnant woman is turned off and the lactate level is dramatically reduced. Because the display 50 shows that the lactate levels of the woman is already very high and rising, such as values above 15 mmol/l, the medical practitioners may learn that there is no longer a need to provide stimulation to the pregnant woman. In this way, the display 50 may be used to prevent the misuse of stimulating substances. The medical practitioner may also use the trends indicated by the data 53, 54, 56 so that the practitioner can see all the data together and take all the information into account before making a decision about what action to take including medication required and the need for performing a caesarian or any other such aided child birth. For example, the cervix dilation data 54 may be compared to a normal cervix dilation curve 55 that applies to most women. The medical practitioner may also use the display 50 to see how the pregnant woman and fetus are reacting to treatment.

The practitioner may take a plurality of measurements of the lactate concentrations 52 at time intervals. The measured lactate concentrations 52 are then presented at the time intervals on the display 50. The lactate concentrations 52 are evaluated to determine whether the lactate concentrations 52 are rising to indicate that an individual lactate threshold value 58 of the pregnant woman has been exceeded. To be able to determine that the individual lactate threshold has been exceeded is particularly important for women who have an unusually high or low lactate threshold.

All the data 52, 53, 54, 56 and other data that have been displayed on the display 50 may be saved for later retrieval together with information of the time the data was measured. The data may be stored together with patient information. This data may be electronically transferred to remote equipment such as electronic medical records by using wireless or wired communication. The device may also be equipped with an automatic decision guiding and alarm system that is based on measured lactate values from mother, measured fetal lactate values, measured fetal pH values. The system may also base decisions and alarms on the opening size of cervix and the progression of the fetus head in the pelvis. Of course, a combination of the above information may be used. The devise 50 should be designed so that it can handle several childbirth processes at the same time in the same device. The stored data in the device may have the ability to enter and present the measured data in electronic medical records.

While the present invention has been described in accordance with preferred compositions and embodiments, it is to be understood that certain substitutions and alterations may be made thereto without departing from the spirit and scope of the following claims.

The invention claimed is:

1. A method of monitoring a childbirth process of a pregnant woman, comprising:
   measuring a lactate concentration in a vaginal fluid of said pregnant woman;
   determining whether the measured lactate concentration is within a lactate threshold interval; and
   subjecting the pregnant woman to alternative child birth options, or stimulation with drugs, when the lactate concentration is outside the lactate threshold interval.

2. The method according to claim 1 wherein the method further comprises stimulating the pregnant woman to give birth when the lactate concentration is less than the lactate threshold interval.

3. The method according to claim 2 wherein the method further comprises determining whether labor is progressing normally after said step of stimulating the woman.

4. The method according to claim 3 wherein the method comprises repeating said step of measuring a lactate concentration in the vaginal fluid of said pregnant woman and said step of determining whether said measured lactate concentration is within the lactate threshold interval when the labor is not progressing normally, and subjecting the pregnant woman to alternative child birth options, or stimulation with drugs, when the lactate concentration is outside the lactate threshold interval.

5. The method according to claim 1 wherein the method further comprises determining whether labor is progressing normally when the lactate concentration measured is within the lactate threshold interval and providing stimulation to the pregnant woman when it is determined that the labor is not progressing normally.

6. The method according to claim 1 wherein the method comprises measuring a plurality of lactate concentrations at a plurality of time intervals and evaluating whether the lactate concentration in the vaginal fluid of the pregnant woman is rising over the time intervals.

7. The method according to claim 1 wherein the method further comprises measuring a lactate concentration in a vaginal fluid of said pregnant woman; determining whether the measured lactate concentration is greater than a predetermined lactate concentration, and determining the pregnant woman's membrane has ruptured and amniotic fluid has passed from an amnion of the pregnant woman if the measured lactate concentration is greater than the predetermined lactate concentration.

8. A method for monitoring a childbirth process of a pregnant woman, comprising:

measuring a lactate concentration in a vaginal fluid from said pregnant woman; and comparing the measured lactate concentration to a predetermined lactate concentration, wherein a measured lactate concentration above said predetermined lactate concentration indicates that the pregnant woman's membrane has ruptured and amniotic fluid has passed from an amnion of the pregnant woman.

9. The method according to claim 8 wherein the method further comprises waiting a waiting period when the lactate concentration is less than the predetermined lactate concentration and again measuring the lactate concentration.

10. The method according to claim 8 wherein the method further comprises waiting a waiting period when the lactate concentration is greater than the predetermined lactate concentration and thereafter determining whether labor is progressing normally following said waiting period.

11. The method according to claim 8 wherein the method further comprises, when labor has not started or is not progressing normally, measuring a lactate concentration in a vaginal fluid of said pregnant woman;

determining whether the measured lactate concentration is within a lactate threshold interval; and subjecting the pregnant woman to alternative child birth options, or stimulation with drugs, when the lactate concentration is outside the lactate threshold interval.

12. The method according to claim 11 wherein the method further comprises stimulating the pregnant woman to give birth when the lactate concentration is less than the lactate threshold interval.

13. The method according to claim 12 wherein the method further comprises determining whether labor is progressing normally after said step of stimulating the pregnant woman.

14. The method according to claim 13 wherein the method comprises repeating said step of measuring a lactate concentration in the vaginal fluid of said pregnant woman and said step of determining whether said measured lactate concentration is within the lactate threshold interval when the labor is not progressing normally, and subjecting the pregnant woman to alternative child birth options, or stimulation with drugs, when the lactate concentration is outside the lactate threshold interval.

15. The method according to claim 11 wherein the method further comprises determining whether labor is progressing normally when the lactate concentration measured is within the lactate threshold interval and providing stimulation to the pregnant woman when it is determined that the labor is not progressing normally.

16. The method according to claim 11 wherein the method comprises measuring a plurality of lactate concentrations at a plurality of time intervals and evaluating whether the lactate concentration in the vaginal fluid of the pregnant woman is rising over the time intervals.

* * * * *